United States Patent
Grahn et al.

(10) Patent No.: US 10,065,021 B2
(45) Date of Patent: Sep. 4, 2018

(54) CONVECTION-ENHANCED DELIVERY CATHETER WITH REMOVABLE STIFFENING MEMBER AND METHOD FOR USING SAME

(75) Inventors: Amy Grahn, Lake Bluff, IL (US); Matthias Luz, Mannheim (DE)

(73) Assignee: MEDGENESIS THERAPEUTIX, INC., Victoria, British Columbia (CA)

( * ) Notice: Subject to any disclaimer, the term of this patent is extended or adjusted under 35 U.S.C. 154(b) by 887 days.

(21) Appl. No.: 12/600,636

(22) PCT Filed: May 16, 2008

(86) PCT No.: PCT/US2008/064011
§ 371 (c)(1),
(2), (4) Date: May 7, 2010

(87) PCT Pub. No.: WO2008/144585
PCT Pub. Date: Nov. 27, 2008

(65) Prior Publication Data
US 2010/0217228 A1    Aug. 26, 2010

Related U.S. Application Data (60) Provisional application No. 60/930,721, filed on May 17, 2007.

(51) Int. Cl.
*A61M 25/00* (2006.01)
*A61M 25/01* (2006.01)

(52) U.S. Cl.
CPC .... *A61M 25/0102* (2013.01); *A61M 25/0068* (2013.01); *A61M 2025/0004* (2013.01);
(Continued)

(58) Field of Classification Search
CPC .......... A61M 25/0068; A61M 25/0102; A61M 2025/0004; A61M 2025/0042;
(Continued)

(56) References Cited

U.S. PATENT DOCUMENTS 4,323,071 A * 4/1982 Simpson et al. ............. 606/194
4,448,532 A   5/1984 Joseph et al.
(Continued)

FOREIGN PATENT DOCUMENTS

GB    1255551     12/1971
JP    59-088092    5/1984
(Continued)

OTHER PUBLICATIONS

Bankiewicz, K., et al., "Convection-enhanced delivery of AAV vector in parkinsonian monkeys; in vivo detection of gene expression and restoration of dopaminergic function using pro-drug approach," Exp. Neurol. 164(1):2-14 (2000).
(Continued)

*Primary Examiner* — Deanna K Hall
(74) *Attorney, Agent, or Firm* — Todd A. Lorenz (57) ABSTRACT

A catheter for delivering an agent to targeted tissue of a mammalian body including a first elongate tubular member having a proximal opening and a distal end wall. A second elongate tubular member having a portion extends through first elongate tubular member and has a distal end extending beyond the end wall. The first and second tubular members form an annular cavity within the first tubular member. A stiffening member has at least a portion disposed within the annular cavity for facilitating accurate placement of the distal end relative to the targeted tissue in the mammalian body and is removeable from the annular cavity after such placement without removal of the second elongate tubular member from the mammalian body. A method is provided.

6 Claims, 4 Drawing Sheets

(52) U.S. Cl.
CPC ............... *A61M 2025/0042* (2013.01); *A61M 2025/0063* (2013.01); *A61M 2025/0188* (2013.01); *A61M 2210/0693* (2013.01)

(58) Field of Classification Search
CPC .. A61M 2025/0063; A61M 2025/0188; A61M 2210/0693; A61M 25/01; A61M 25/0172
USPC .......... 604/158, 500, 528, 913, 177, 103.04, 604/170.01–170.02, 161; 600/585
See application file for complete search history.

(56) References Cited

U.S. PATENT DOCUMENTS

| | | | |
|---|---|---|---|
| 4,775,371 | A | 10/1988 | Mueller, Jr. |
| 4,884,573 | A | 12/1989 | Wijay et al. |
| 4,978,334 | A | 12/1990 | Toye et al. |
| 5,273,052 | A * | 12/1993 | Kraus et al. .................. 600/585 |
| 5,279,551 | A * | 1/1994 | James ............................ 604/44 |
| 5,318,542 | A * | 6/1994 | Hirsch et al. ................. 604/161 |
| 5,382,238 | A | 1/1995 | Abrahamson et al. |
| 5,720,720 | A | 2/1998 | Laske et al. |
| 6,042,579 | A | 3/2000 | Elsberry |
| RE37,410 | E | 10/2001 | Brem |
| 6,309,634 | B1 | 10/2001 | Bankiewicz et al. |
| 6,676,900 | B1 * | 1/2004 | Divino et al. .................. 422/45 |
| 6,859,660 | B2 | 2/2005 | Vilsmeier |
| 6,994,693 | B2 * | 2/2006 | Tal ..................... A61B 17/3415 604/158 |
| 7,182,944 | B2 | 2/2007 | Bankiewicz |
| 7,241,283 | B2 | 7/2007 | Putz |
| 7,341,577 | B2 | 3/2008 | Gill |
| 7,371,225 | B2 | 5/2008 | Oldfield et al. |
| 7,815,623 | B2 | 10/2010 | Bankiewicz et al. |
| 2002/0114780 | A1 | 8/2002 | Bankiewicz et al. |
| 2004/0006316 | A1 * | 1/2004 | Patton ........................... 604/244 |
| 2004/0092879 | A1 | 5/2004 | Kraus et al. |
| 2004/0209810 | A1 | 10/2004 | Gill et al. |
| 2005/0080398 | A1 * | 4/2005 | Markel ............. A61M 25/0014 604/508 |
| 2005/0112065 | A1 | 5/2005 | Drummond et al. |
| 2005/0154297 | A1 | 7/2005 | Gill |
| 2007/0088295 | A1 | 4/2007 | Bankiewicz |
| 2008/0045894 | A1 * | 2/2008 | Perchik ............. A61M 25/0194 604/96.01 |

FOREIGN PATENT DOCUMENTS

| | | |
|---|---|---|
| JP | 59-105141 | 6/1984 |
| JP | 09-253214 | 9/1997 |
| WO | WO 95/05864 | 3/1995 |
| WO | WO 96/00597 A1 | 1/1996 |
| WO | WO 99/04849 | 2/1999 |
| WO | WO 02/053205 | 7/2002 |
| WO | WO 04/031348 | 4/2004 |
| WO | WO 06/015091 | 2/2006 |

OTHER PUBLICATIONS

Bankiewicz, K., et al., "Focal striatal dopamine may potentiate dyskinesias in parkinsonian monkeys," Exp. Neurol. 197:363-72 (2006).
Bankiewicz, K., et al., "Practical Aspects of the Development of ex Vivo and in Vivo Gene Therapy for Parkinson's Disease," Experimental Neurology, 144:147-156 (1997).
Bruce, et al., "Intracerebral clysis in a rat glioma model," Neurosurgery 46(3):683-91 (2000).
Chen, et al., "Combination Therapy with Irinotecan and Protein Kinase C Inhibitors in Malignant Glioma," Cancer 97(9 Suppl):2363-73 (2003).
Chen, et al., "Surface properties, more than size, limiting convective distribution of virus-sized particles and viruses in the central nervous system," J. Neurosurg. 103:311-19 (2005).
Chen, et al., "Variables affecting convection-enhanced delivery to the striatum: a systematic examination of a rate of infusion, cannula size, infusate concentration, and tissue-cannula sealing time," J. Neurosurg. 90(2):315-20 (1999).
Cunningham, et al., "Distribution of AAV-TK following intracranial convection-enhanced delivery into rats," Cell Transplant 9(5):585-94 (2000).
Extended European search report, European Patent Office, regarding European Patent Application No. 08755793, held in the name of Medgenesis Therapeutix, Inc., dated Dec. 28, 2010.
European examination report, European Patent Office, regarding European Patent Application No. 08755793, held in the name of Medgenesis Therapeutix, Inc., dated Aug. 30, 2011.
Groothuis, "The blood-brain and blood-tumor barriers: a review of strategies for increasing drug delivery," Neurooncol 2(1):45-59 (2000).
Hadaczek, et al., "Convection-enhanced delivery of adeno-associated virus type 2 (AAV2) in the striatum and transport of AAV2 within monkey brain," Human Gene Therapy 17:1-12 (2006).
Hadaczek, et al., "The perivascular pump driven by arterial pulsation is a powerful mechanism for the distribution of therapeuctic molecules within the brain," Mol. Ther. 14(1):69-78 (2006).
Haroun, et al., "Local drug delivery," Current Opinion in Oncology 12:187-93 (2000).
International Search Report, United States Patent and Trademark Office, regarding International Patent Application No. PCT/US08/64011, held in the name of Medgenesis Therapeutix, Inc., dated Sep. 23, 2008.
Krauze, et al., "Effects of the perivascular space on convection-enhanced delivery of liposomes in primate putamen," Experimental Neurology 196:104-11 (2005).
Krauze, et al., "Real-time imaging and quantification of brain delivery of liposomes," Pharmaceutical Research 23:2493-2504 (2006).
Krauze, et al., "Reflux-free cannula for convection-enhanced high-speed delivery of therapeutic agents," J. Neurosurg. 103:923-29 (2005).
Laske, et al., "Chronic interstitial infusion of protein to primate brain: determination of drug distribution and clearance with single-photon emission computerized tomography imaging," J. Neurosurg 87(4):586-94 (1997).
Lonser, et al., "Successful and safe perfusion of the primate brainstem: in vivo magnetic resonance imaging of macromolecular distribution during infusion," J. Neurosurg 97(4):905-13 (2002).
Mamot, et al., "Extensive distribution of liposomes in rodent brains and brain tumors following convection-enhanced delivery," J Neurooncol 68(1):1-9 (2004).
Mardor, et al., "Monitoring response to convection-enhanced taxol delivery in brain tumor patients using diffusion-weighted magnetic resonance imaging," Cancer Research 61(13):4971-3 (2001).
Morrison, et al., "Focal delivery during direct infusion to brain: role of flow rate, catheter diameter, and tissue mechanics," Am. J. Physiol. Regul. Integr. Comp. Physiol. 277:R1218-R1229 (1999).
Morrison, et al., "High-flow microinfusion: tissue penetration and pharmacodynamics," Am J. Physiol. 266(1 Pt. 2):R292-305 (1994).
Nicholson, et al., "Extracellular space structure revealed by diffusion analysis," Trends Neurosci 21:207-15 (1998).
Pardridge, "Drug delivery to the brain," J Cereb Blood Flow Metab 17:713-31 (1997).
Pardridge, "The blood-brain barrier: bottleneck in brain drug development," NeuroRx 2:3-14 (2005).
Patel, et al., "Intraputamenal infusion of glial cell line-derived neurotrophic factor in PD: a two-year outcome study," Ann. Neurol., 57:298-302 (2005).
Saito, et al., "Convection-enhanced delivery of tumor necrosis factor-related apoptosis-inducing ligand with systemic administration of temozolomide prolongs survival in an intracranial glioblastoma xenograft model," Cancer Res 64(19):6858-62 (2004b).
Saito, et al., "Distribution of liposomes into brain and rat brain tumor models by convection-enhanced delivery monitored with magnetic resonance imaging," Cancer Research 64:2572-79 (2004).

(56) References Cited

OTHER PUBLICATIONS

Saito, et al., "Gadolinium-loaded liposomes allow for real-time magnetic resonsance imaging of convection-enhanced dlievery in the primate brain," Exp Neurol. 196(2):381-9 (2005).
Vogelbaum, J., "Convection enhanced delivery for the treatment of malignant gliomas: symposium review," J. Neuro-oncology 73:57-69 (2005).
Westphal, et al., "Perspective of cellular and molecular neurosurgery," J. Neuro-oncology 70(2):255-69 (2004).

* cited by examiner

CONVECTION-ENHANCED DELIVERY CATHETER WITH REMOVABLE STIFFENING MEMBER AND METHOD FOR USING SAME

SCOPE OF THE INVENTION

The present invention relates to catheters and more particularly to convection-enhanced delivery catheters.

BACKGROUND

Convection enhanced delivery, or CED, is a local delivery technique for the distribution of infused compounds. CED uses bulk flow to deliver small or large molecules into targeted sites, for example in the brain, through stereotactically positioned catheters. Bypassing the blood brain barrier, CED can expose tumors and other target tissues to therapeutic agents, minimizing systemic exposure so as to result in fewer systemic side effects.

A number of factors are believed to significantly impact the success of local drug delivery via CED. The first such factor is backflow along the outer surface of the infusion catheter, which typically occurs with larger catheter diameters and higher infusion rates. The second such factor is the intrusion of air and pressure peaks that can arise from disconnecting and reconnecting the system after the catheter has been placed. The third such factor is the anatomic accuracy of the catheter placement and the prevention of leakage into the cerebrospinal fluid compartment of the infusate.

SUMMARY OF THE INVENTION

A catheter for delivering an agent to targeted tissue of a mammalian body is provided and includes a first elongate tubular member having a proximal opening and a distal end wall. A second elongate tubular member having a portion extends through first elongate tubular member and has a distal end extending beyond the end wall. The first and second tubular members form an annular cavity within the first tubular member. A stiffening member has at least a portion disposed within the annular cavity for facilitating accurate placement of the distal end relative to the targeted tissue in the mammalian body and is removeable from the annular cavity after such placement without removal of the second elongate tubular member from the mammalian body. A method is provided.

DESCRIPTION OF THE INVENTION

The catheter of the present invention serves as a dedicated CED catheter for temporary or permanent implantation in the mammalian body, preferably the brain. One embodiment of the catheter system 21 of the present invention, shown in FIG. 1, comprises a catheter 22 having a main catheter tube 23 or first elongate tubular member guiding a micro infusion catheter tube 24 or second elongate tubular member within the lumen 26, preferably its elongate central lumen or passageway, of the main catheter tube. The micro infusion catheter tube 24 is also provided with a central lumen or passageway 27. The main tube 23 has a distal extremity 28 having at least one end wall 29 that is preferably planar and extending perpendicularly of the longitudinal axis of the main tube. The distal extremity 31 of the micro infusion tube extends through the main tube and is preferably concentrically disposed relative to the main tube, the inner diameter of the central lumen 26 of the main tube 23 being wider or larger than the outer diameter of the micro infusion catheter tube 24 so as to form an annular cavity or space between the main tube and the distal extremity of the micro infusion tube. Both single lumen tubes 23 and 24 are connected at the distal end 28 of the main catheter tube 23 so that the lumens of the tubes 23 and 24 are not communicating and the lumen 26 of the main catheter tube ends blindly at the connection site of the tubes 23 and 24. The distal end of the micro infusion tube extends through and beyond the distal end of the main catheter tube to create a shoulder or step 32 at the catheter tip suitable to reduce backflow of fluid along the outer surface of the catheter. More specifically, the distal extremity or end 31 of the micro infusion tube 24 is secured to the end wall 29 of the main tube 23, by any suitable means such as an adhesive or welding, and extends distally of such end wall.

Figure 1:
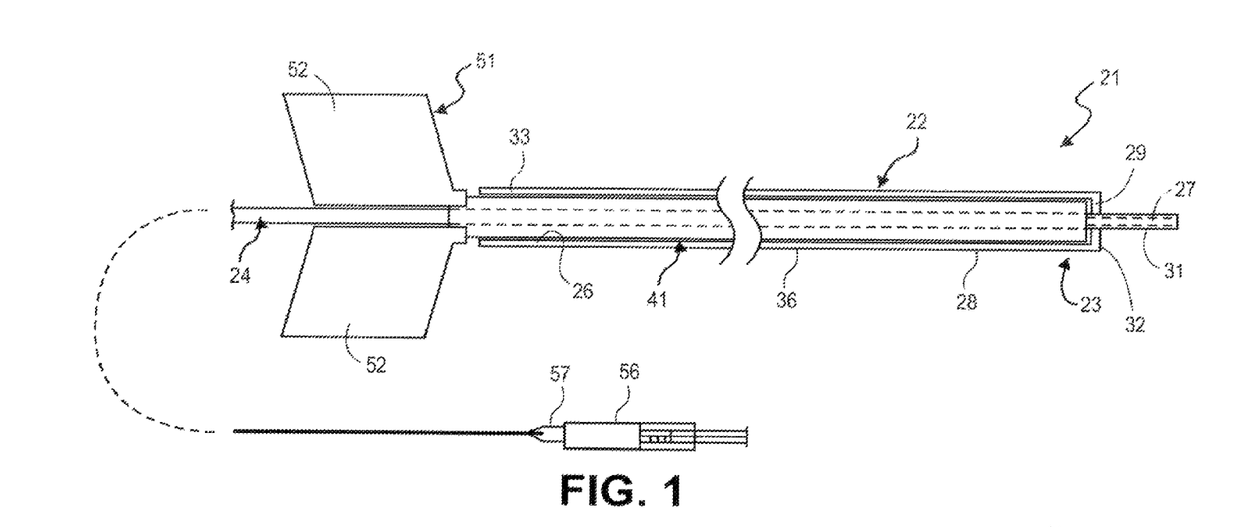
FIG. 1 is a plan view of catheter system having a convection-enhanced delivery catheter of the present invention.

The main tube 23 of the catheter can be made from any suitable material such as plastic and more preferably polyether block amide or aliphatic polyether polyurethane. The main tube has a length so that when the distal end 28 of the main tube is in the vicinity of the tissue being treated the proximal extremity or end 33 of the main tube is outside of the body and accessible by the operator of the catheter. In one preferred embodiment, the main tube 23 has a length ranging from 200 to 300 millimeters and preferably approximately 270 millimeters, a nominal wall thickness ranging from 0.15 to 1.0 millimeters and preferably approximately 0.5 millimeters, an internal diameter ranging from 0.5 to 1.25 millimeters and preferably approximately 1.00 millimeters and an external diameter ranging from 1.00 to 1.75 millimeters and preferably approximately 1.50 millimeters. The main tube can be of any suitable hardness and in one preferred embodiment has a hardness ranging from 83 Shore A to 40 Shore D. The micro infusion tube 24 can be made from any suitable material such as plastic and more preferably polyimide and can be of any suitable size. In one preferred embodiment, the micro infusion tube has a length of approximately 600 millimeters, a nominal wall thickness ranging from 0.05 to 0.60 millimeters and preferably approximately 0.48 millimeters, an internal diameter ranging from 0.08 to 0.25 millimeters and preferably approximately 0.12 millimeters and an external diameter ranging from 0.30 to 0.70 millimeters and preferably approximately 0.60 millimeters. In one preferred embodiment, the distal extremity or end 31 of the micro infusion tube extends beyond the distal end 28 of the main tube 23 a distance ranging from four to 15 millimeters and preferably approximately five millimeters.

A scale (not shown) is preferably provided on the outer surface 36 of the main tube 23 to enable the surgeon or other operator to place the catheter 22 at the correct depth in the tissue to be treated, such as brain tissue of a mammalian body. Additionally, the material of the main catheter is preferably suitable to be marked with a sterile marker pen to mark the planned depth of advance prior to such placement.

Figure 2:
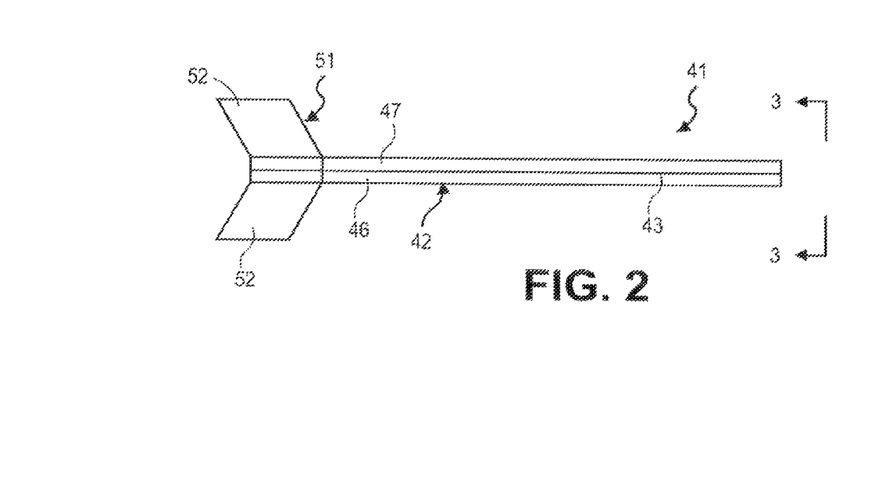
FIG. 2 is a plan view of the stiffening member of the convection-enhanced delivery catheter of FIG. 1.
Figure 3:
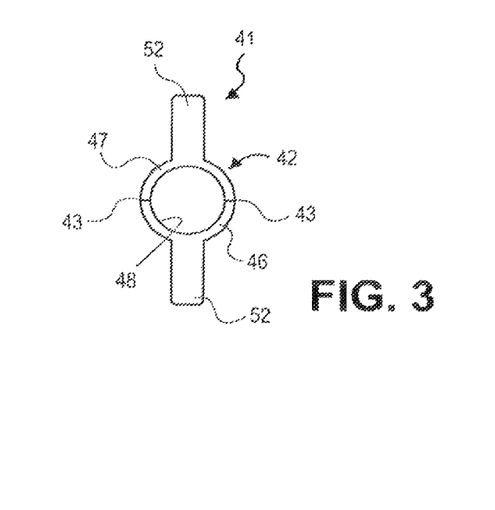
FIG. 3 is an end view of the stiffening member of FIG. 2 taken along the line 3-3 of FIG. 2.
Figure 4:
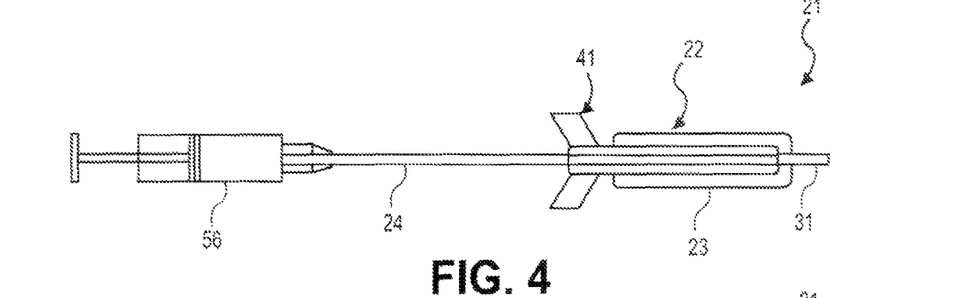
FIG. 4 is a schematic view of the catheter system of FIG. 1 with the stiffening member in a first or operational position within the convection-enhanced delivery catheter.

To enhance the stability of the catheter during placement and aid in maintaining the catheter on the desired trajectory during such placement, the catheter further includes a stiffening member 41 (see FIGS. 1-3). The stiffening member or element is preferably removable after placement of the catheter for treatment. In one preferred embodiment, the stiffening member or split cannula 41 is in the form of a tubular member 42 that is removeably disposed within the annular cavity provided between the main tube 23 and the distal extremity of the micro infusion tube 24. The stiffening member is shown in the drawings as a split cannula which is circular in cross section, as shown in FIG. 3, and more specifically has a cross section approximating the cross section of the annular cavity in the main tube. In one embodiment, the tubular member 42 of the split cannula has two predetermined longitudinal break lines 43 at an angle of 180° to each other, shown in FIGS. 2-3, where the material is thinned out to allow separation of the tubular member 42 into two parts, that is first and second elongate portions 46 and 47. Each of the elongate portions, as shown in FIG. 3, has a semicircular cross section. In another embodiment, not shown, the tubular member of the split cannula 41 is made from metal tape formed into a tube with a very small gap separating the longitudinal sides of the tape. Opposite of the gap a predetermined breaking line is manufactured in the tape.

A central lumen 48 extends through the split cannula and is sized and shaped to receive a portion of the distal extremity 31 of the micro infusion tube 24. In one preferred embodiment, the split cannula 41 has a length ranging from 250 to 350 millimeters and preferably approximately 305 millimeters, a nominal wall thickness of approximately 0.2 millimeters, an internal diameter ranging from 0.40 to 0.80 millimeters and preferably approximately 0.70 millimeters and an external diameter of approximately 0.9 millimeters.

The proximal end 51 of the split cannula extends proximally of the proximal end 33 of the main tube and the opening of the annular cavity in the main tube so as to be accessible by the operator when the catheter 22 has been properly placed within the mammalian body for treatment. The proximal end of the split cannula is sized and shaped so as to be easily grasped by the operator and in one preferred embodiment the proximal end 51 of each of the first and second elongate portions 46 and 47 of the split cannula 41 is provided with a fin or handle 52 extending proximally and radially outwardly from the semicircular central and proximal portions of such elongate portion. Each of the first and second elongate portions of the split cannula can be made from any suitable material such as a cobalt-chromium-nickel alloy known as Phynox. The fins or wings 42 can be made from any suitable material such as plastic.

Catheter system 21 further includes a supply of a suitable agent for delivery to or near the targeted tissue. Such supply can be in the form of a syringe 56 that is fluidly coupled to the proximal end of the micro infusion catheter tube 24, for example by means of luer lock adapter 57.

Figure 5:
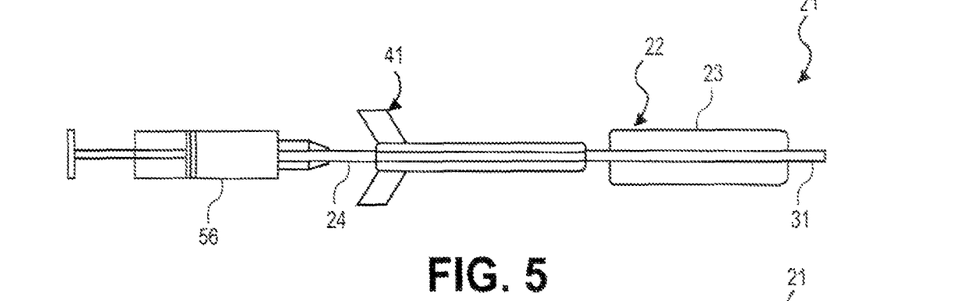
FIG. 5 is a schematic view, similar to FIG. 4, with the stiffening member in a second position removed from the convection-enhanced delivery catheter.
Figure 6:
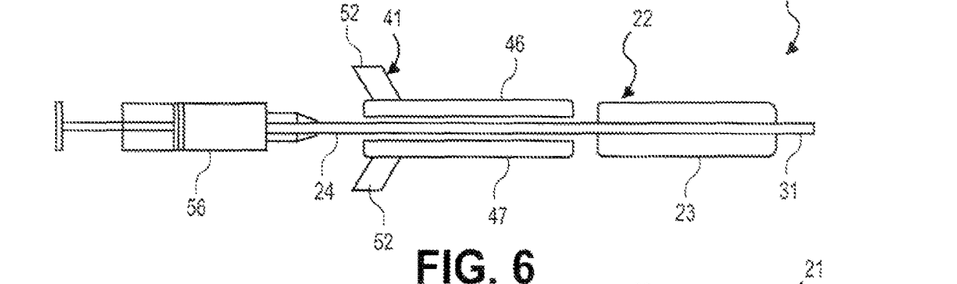
FIG. 6 is a schematic view, similar to FIG. 4, with the stiffening member is a third or split position removed from the convection-enhanced deliver catheter.
Figure 7:
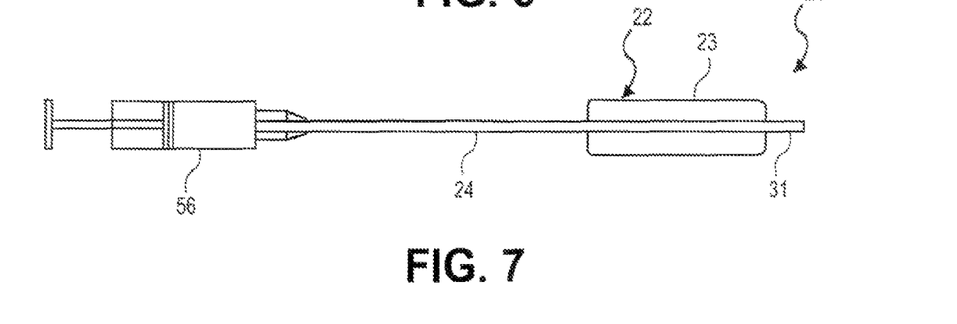
FIG. 7 is a schematic view, similar to FIG. 4, without the stiffening member.

In operation and use of catheter 22 in a cranial procedure, the distal end 28 of the catheter is advanced through the cerebral tissue until the distal end 31 of the micro infusion tube is disposed in the target tissue to be treated. The micro infusion tube 24 extends through adjacent or intermediate tissue to the center of the targeted tissue. The end wall or step abuts the intermediate tissue. After placement of the catheter 22, the fins or handles 52 located on the proximal ends 51 of the elongate portions 46 and 47 of the split cannula 41 are pulled proximally by the operator while the main tube of the catheter is kept in position either by another hand of the operator or by other suitable means. Once the split cannula 41 has been completely pulled proximally out of the annular cavity of the main tube 23, as shown in FIG. 5, the split cannula is torn apart or split in half, as shown in FIG. 6, so that each of the first and second elongate portions 46 and 47 of the split cannula can be pulled radially away from the micro infusion tube 24 and thus removed from the catheter 22, as shown in FIG. 7. The micro infusion tube 24 of the catheter remains connected to the syringe 56 or other suitable infusion source, for example via the luer-lock adapter 57 that is attached to the proximal end of the micro infusion tube of the catheter.

The agent is delivered from a syringe or other supply through the central passageway or lumen 27 of the micro infusion tube 24 to the targeted tissue. The engagement of the end wall 29 of the main tube 23 of the catheter with the targeted tissue forms a barrier which inhibits any agent which may travel backwards or proximally along the exterior of the distal end 31 of the micro infusion tube 24 extending distally of the end wall from traveling further proximally along the exterior cylindrical or outer surface 35 of the main tube 23 of the catheter 22.

Using the split cannula 41 as described allows placing a fully primed catheter system 21, which can include the syringe 56, without any reconnection procedures between the syringe or other infusion source 56 and the catheter 22, thereby reducing the risk of air intrusion and pressure peaks in the system 21. By so reducing the likelihood of air intrusion into the micro infusion tube 24, the catheter 22 and method of the invention inhibit the formation of air bubbles in the targeted tissue. Such air bubbles can undesirably reduce the delivery of the agent to the targeted tissue, for example by blocking access of the agent to the targeted tissue and by causing the agent to backflow along the outer surface 36 of the catheter 22 away from the targeted tissue.

After the placement procedure for the catheter 22 has been completed and the split cannula 41 removed from the catheter 22, the distal extremity 28 of the catheter, including the main tube 23 and the distal extremity 31 of the micro infusion tube 24, is flexible. This minimizes the risk of catheter dislocation and allows subcutaneous fixing of the catheter 22 on the skull of the patient.

Figure 8:
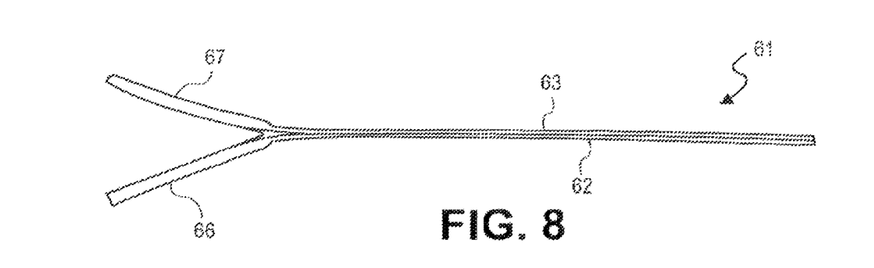
FIG. 8 is another embodiment of the stiffening member of the present invention.

Another embodiment of the stiffening member of the present invention is illustrated in FIG. 8. Stiffening member or split cannula 61 illustrated in FIG. 8 includes first and second elongate portions 62 and 63 substantially similar to the elongate portions 46 and 47 of the split cannula 41. First and second protective tubes 66 and 67, which serve as handles, are glued or otherwise secured to the proximal end of the respective first and second elongate portions 62 and 63 of the split cannula. The tubes or handles 66 and 67 are each made of any suitable material such as plastic.

Figure 9:
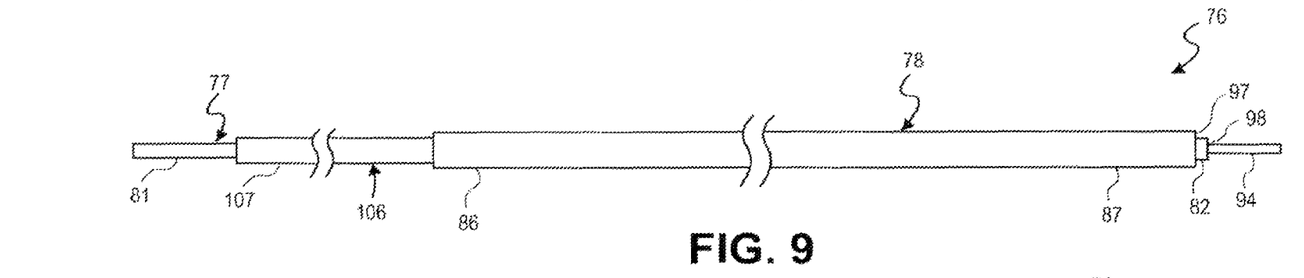
FIG. 9 is a plan view of another embodiment of a convection-enhanced delivery catheter of the present invention.
Figure 10:
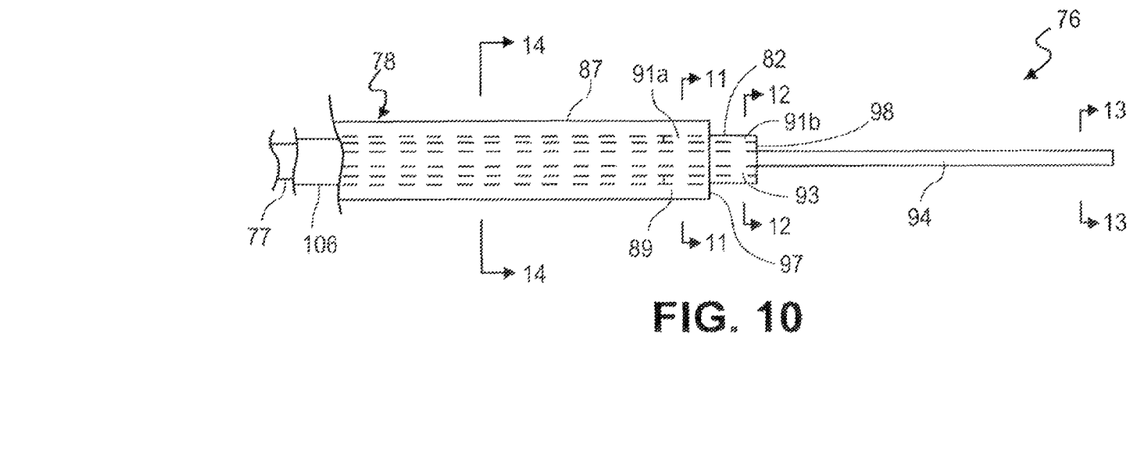
FIG. 10 is an enlarged view of the distal end of the convection-enhanced delivery catheter of FIG. 9.
Figure 11:
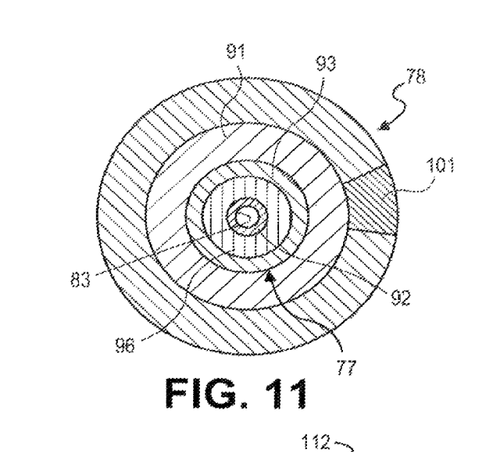
FIG. 11 is a cross-sectional view of the convection-enhanced delivery catheter of FIG. 9 taken along the line 11-11 of FIG. 10.
Figure 12:
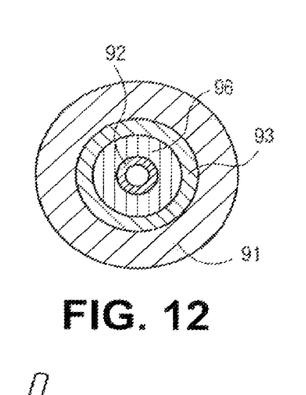
FIG. 12 is a cross-sectional view of the convection-enhanced delivery catheter of FIG. 9 taken along the line 12-12 of FIG. 10.
Figure 13:
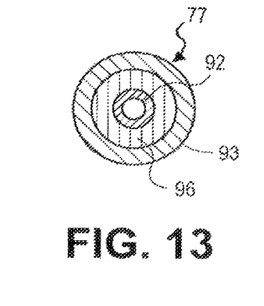
FIG. 13 is a cross-sectional view of the convection-enhanced delivery catheter of FIG. 9 taken along the line 13-13 of FIG. 10.

Another embodiment of the catheter system of the present invention is shown in FIGS. 9-15. A convection-enhanced delivery catheter 76 having a micro infusion catheter tube or first elongate tubular member 77, and a guiding catheter tube or second elongate tubular member 78 outside of the outer cylindrical surface of the micro infusion catheter 77, are provided as illustrated in FIGS. 9 and 10. The micro infusion catheter 77 has a proximal extremity 81 and a distal extremity 82 and a central lumen or passageway 83 extending longitudinally from the proximal extremity to the distal extremity. Similarly, the guiding catheter tuber 78 has a proximal extremity 86 and a distal extremity 87 and a central lumen or passageway 88 extending longitudinally from the proximal extremity 86 to the distal extremity 87. The micro infusion catheter tube 88 is preferably concentrically disposed relative to the guiding catheter tube 78 whose inner diameter is wider or larger than the outer diameter of the micro infusion catheter tube so as to form an annular cavity or space, illustrated in FIG. 14, between the micro infusion catheter tube and the guiding catheter tube. Both single lumen tubes 77 and 78 are connected at the distal extremity or end 87 of the guiding catheter tube 78 so that the lumens of the tubes 77 and 78 are not communicating and the lumen 88 of the guiding catheter tube ends blindly at a distal end wall 89 to form the connection site. More specifically, the distal end 82 of the micro infusion tube is secured to the end wall 89 of the guiding catheter tube by means of any suitable filler material 91 such as tecoflex as shown in FIGS. 10 and 11. The distal filler 91 extends over a suitable length of for example two millimeters. A first portion 91a of the distal filler extends over a suitable length, for example approximately one millimeter, and secures the micro infusion catheter to the guiding catheter, and a second portion 91b of the distal filler extends distally beyond the guiding catheter 78 a suitable length, for example one millimeter, as shown in FIG. 10.

The guiding catheter tube can be made from any suitable material such as plastic and more preferably tecoflex. The micro infusion tube of the catheter can be made from any suitable material such as plastic. In one preferred embodiment, the wall of the micro infusion catheter tube 77 is a layered structure, as shown in FIGS. 11-14, that includes a first or internal layer or liner 92 made from any suitable material such as polyimide and a second or external layer 93, also referred to as the protective tube, made from any suitable material such as polyetheramide. The tubular internal liner 92 extends the length of the micro infusion catheter from the proximal end 82 to the distal end of the catheter tip 94. The external layer or protective tube 93 extends distally through the end wall 89 of the guiding catheter tube to the distal end of the distal filler portion 91b, as illustrated in FIG. 10. The annular space between the two layers 92 and 93 is filled with a third layer made from polyimide, also referred to as the proximal filler and not shown in the drawings, extending over a suitable length ranging from ten to 30 millimeters and more preferably approximately 15 millimeters at the proximal end 81 of the micro infusion tube catheter 77. The central portion or main part of the micro infusion catheter tube, between the two ends 81 and 82, is without an additional third layer so as to be an annular space (not shown). At distal extremity or end 82 of the micro infusion catheter, a suitable material such as fused silica is inserted as a third layer or tube 96 between the inner and outer layers 92 and 93. The central layer 96 can extend over a total length ranging from five to 20 millimeters and more preferably approximately 12 millimeters. Approximately half of the length of the central layer 96 extends distally of the distal end of the outer layer 93 to form the catheter tip 94 of the micro infusion catheter tube 77 as shown in FIGS. 9 and 10. The use of fused silica as the central layer 96 at the distal end 82 of the micro infusion catheter tube provides sufficient stiffness to the catheter tip to allow penetrating highly compact or elastic tissues.

The distal extremity 82 of the micro infusion tube 77, together with the distal filler 91, extends through the distal end 87 of the guiding catheter tube 78. By ending before the distal end of both the micro infusion catheter tube 77 and the distal filler 91, the guiding catheter tube creates a first step or first annular end surface 97 a distance ranging from five to 15 millimeters and more preferably approximately six millimeters from the distal end of the catheter tip 94 of the micro infusion catheter tube 77. The first annular end surface 97 has a radial dimension measured from the outer cylindrical surface of the distal filler 91 to the outer cylindrical surface of the guiding catheter tube 78 ranging from 0.50 to 0.70 millimeters and preferably approximately 0.61 millimeters. The catheter tip 94 of the micro infusion tube 77 extends through the common distal end of the distal filler 91 and the protective tube 93 as shown in FIG. 10. By ending before the distal end of the micro infusion catheter tube, the distal filler and protective tube together create a second step or second annular end surface 98 a distance ranging from four to 14 millimeters and more preferably approximately five millimeters from the distal end of the micro infusion catheter tube 77. The second annular end surface 98 has a radial dimension measured from the outer cylindrical surface of the central layer 96 to the outer cylindrical surface of the distal filler 91 ranging from 0.40 to 0.60 millimeters and preferably approximately 0.53 millimeters. Together, the first and second steps at the tip of the catheter are designed to reduce or eliminate backflow of fluid along the outer surface of the catheter 76 and simultaneously minimize trauma to tissue. The complete two-step design of the tip of the catheter 76 is shown in FIGS. 9 and 10.

The catheter 76 has a length so that when the distal end 82 of the micro infusion catheter tube is in the vicinity of the tissue being treated, the proximal end of the catheter 76 is outside of the body so that the proximal end 86 of the guiding catheter tube 78 and the proximal end 81 of the micro infusion catheter tube 77 are both easily accessible by the operator of the catheter. In one preferred embodiment, the micro infusion catheter tube 77 has a length of approximately 312 millimeters, a total nominal wall thickness of approximately 0.48 millimeters, an internal diameter of approximately 0.12 millimeters and an external diameter of approximately 0.60 millimeters. In one preferred embodiment, the total length of the protective tube 93 of the micro infusion catheter tube ranges from 302 to 308 millimeters, leaving the catheter tip 94 unprotected by the tube 93 over a distance ranging from four to ten millimeters and preferably approximately five millimeters. In such one preferred embodiment, the protective tube has a nominal wall thickness of approximately 024 millimeters, an internal diameter of approximately 0.12 millimeters and an external diameter of approximately 0.36 millimeters. The guiding catheter tube 78 can be of any suitable size. In one preferred embodiment, the guiding catheter tube has a length of approximately 270 millimeters, a nominal wall thickness of approximately 0.5 millimeters, an internal diameter of approximately 1.00 millimeters and an external diameter of approximately 1.50 millimeters. The wall thickness of the wall elements or layers of the micro infusion catheter tube and the guiding catheter tube are shown in cross section in FIGS. 11-14.

Figure 14:
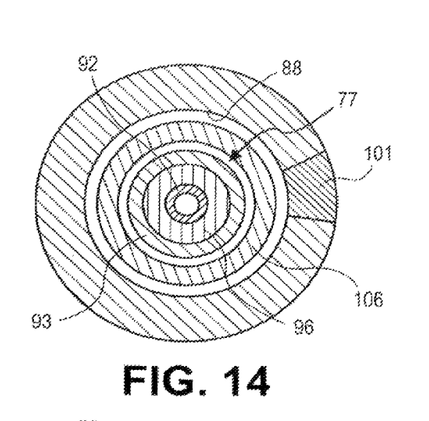
FIG. 14 is a cross-sectional view of the convection-enhanced delivery catheter of FIG. 9 taken along the line 14-14 of FIG. 10.

A radio opaque scale 101 is preferably provided on the outer surface of the guiding catheter tube 78, as shown in FIGS. 11 and 14, to enable the surgeon or other operator to place the catheter 76 at the correct depth in the tissue to be treated, such as brain tissue of a mammalian body. Additionally, the material of the guiding catheter tube 78 is preferably suitable to be marked with a sterile marker pen to mark the planned depth of advance prior to such placement. The radio opaque scale can be visualized by computed tomography (CT) imaging the brain tissue after catheter implantation allowing the surgeon or operator to determine the exact location of the catheter 76.

To enhance the stability of the catheter 76 during placement and aid in maintaining the catheter on the desired trajectory during such placement, the catheter can further include a stiffening member 106 having a proximal end or extremity 107. The stiffening member or element 106 is preferably removable after placement of the catheter for treatment. In one preferred embodiment, the stiffening member is in the form of a tubular member that is removeably disposed within the annular cavity provided between the micro infusion catheter tube 77 and the guiding catheter tube 78, as shown in FIGS. 9, 10 and 14. The stiffening member or hollow stylet 106 is circular in cross section and more specifically has a cross section approximating the cross section of the lumen 88 of the guiding catheter tube 78. In one embodiment, the hollow stylet 106 is made from stainless steel or other similar material formed into a tube, which inhibits bending of the stylet 106 and thus provides rigidity to the catheter 76. A central lumen (not shown) extends through the hollow stylet 106 and is sized and shaped to receive a portion of the micro infusion tube 77. The outer diameter of the hollow stylet allows the guiding catheter tube 78 to slideably receive a portion of the hollow stylet providing a cavity that holds the hollow stylet in place by means of a friction fit during catheter placement. In one preferred embodiment, the hollow stylet has a length of approximately 305 millimeters, a nominal wall thickness of approximately 0.2 millimeters, an internal diameter of approximately 0.7 millimeters and an external diameter of approximately 0.9 millimeters. The proximal end 107 of the hollow stylet extends proximally approximately 25 millimeters from the proximal end 86 of the guiding catheter tube 77, that is from the proximal end of the opening of the annular cavity between the micro infusion catheter and the guiding catheter tube, so as to be accessible by the operator when the catheter 76 has been properly placed within the mammalian body for treatment. The proximal end 107 of the hollow stylet 106 is sized and shaped so as to be easily grasped by the operator.

Figure 15:
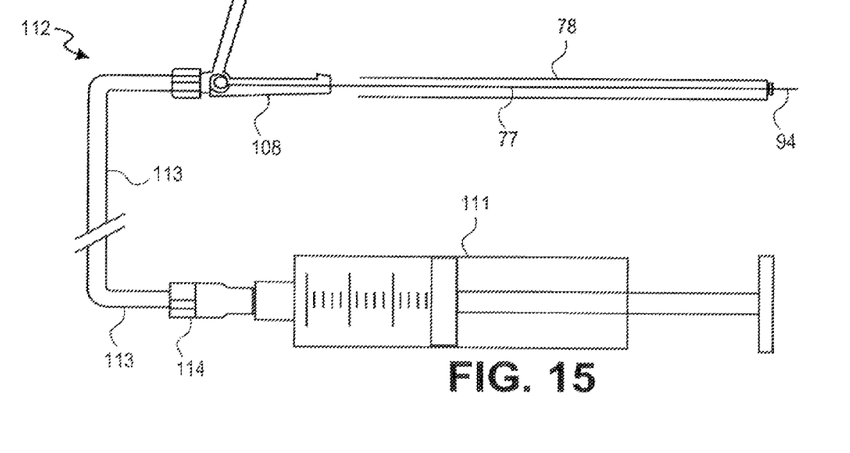
FIG. 15 is a schematic plan view of the convection-enhanced delivery catheter of FIG. 9, with the stiffening member removed, being utilized with an infusion system.

In operation and use of catheter 76 in a cranial procedure, after filling the catheter with saline to remove any air and connecting the micro infusion catheter 77 and hollow stylet 106 as shown in FIG. 15 with a suitable capped closed connector 108, such as a Perifix® connector made by B Braun Medical Inc. of Bethlehem, Pa., the distal end of the catheter is advanced through the cerebral tissue until the distal extremity 82 of the micro infusion tube 77 is disposed in the target tissue to be treated. The catheter tip 94 of the micro infusion tube extends through adjacent or intermediate tissue to the center of the targeted tissue. The first and second end surfaces 97 and 98 at the distal end of the catheter 76 abut the intermediate tissue. After placement of the catheter, the click-to-close connector 108 is opened and removed so that the hollow stylet 106 can be pulled proximally over the micro infusion catheter tube 77 by the operator while the guiding catheter tube 78 of the catheter is kept in position either by another hand of the operator or by other suitable means. Once the hollow stylet has been completely pulled proximally out of the annular cavity between the guiding catheter tube 78 and the micro infusion catheter tube 77, the hollow stylet is pulled away from the micro infusion catheter tube and thus removed from the catheter. The micro infusion tube of the catheter is reconnected to the saline primed connector 108 and capped, preventing introduction of air. Three point fixation allows subcutaneous fixing of the catheter 76 on the skull of the patient and the area is properly bandaged until the initiation of drug infusion.

A suitable infusion source or supply in the form of a syringe 111, and a suitable infusion system 112 for use with catheter 76 are shown in FIG. 15. In one preferred embodiment, a drug primed infusion system 112 is prepared in the pharmacy made up of a connector 108 attached to a microbore infusion tubing 112 that is connected to the syringe 111 with a suitable air tight connector 113 such as a microCLAVE® connector made by ICU Medical, Inc. of San Clemente, Calif. The system 112 is primed by using a bolus system on a suitable micro infusion pump (not shown). Once primed, the infusion system 112 is connected to catheter 76 by removal of the existing click-to-close connector 108 and replacing such connector with the drug-primed click-to-close connector 108 attached to the infusion system 112.

A suitable agent is delivered from syringe 111 through the central passageway or lumen 83 of the micro infusion tube 77 to the targeted tissue. The two-step design of first and second end surfaces 97 and 98 at the distal end of the catheter 76 forms a barrier which inhibits any agent which may travel backwards or proximally along the catheter tip 94 from travelling further proximally along the exterior surface of the guiding catheter tube 78 of the catheter.

The utilization of hollow stylet 106 in the manner described above permits placing a fully primed catheter 76 connected to a primed click-to-close connector 108 in the closed position thereby reducing the risk of air intrusion and pressure peaks in the system. Removal of the connector 108 after the catheter 76 has been properly positioned can be done without significantly increasing the risk of air intrusion because the capillary pressure in the small lumen of the micro infusion catheter 77 is high and the tip of the micro infusion catheter 77 is occluded by tissue. By so reducing the likelihood of air intrusion into the micro infusion tube 77, the catheter 76 and method of the invention inhibit the formation of air bubbles in the targeted tissue. Such air bubbles can undesirably reduce the delivery of the agent to the targeted tissue, for example by blocking access of the agent to the targeted tissue and by causing the agent to backflow along the outer surface of the catheter 76 away from the targeted tissue.

After the placement procedure for catheter 76 has been completed and the hollow stylet 106 removed from the catheter, the micro infusion tube is flexible. This minimizes the risk of catheter dislocation and allows subcutaneous fixing of the catheter on the skull of the patient without encountering the risk of kinking or breakage of the catheter.

The major objective of the intracerebral catheter of the present invention is to provide a predictable and reproducible drug distribution in a defined target area within brain tissue. A high accuracy in terms of catheter placement as well as a dedicated design to minimize backflow along the outer surface of the catheter facilitates the achievement of such objective. To avoid air bubbles within the infusion line leading to an unpredictable drug distribution, the infusion line is primed before the actual placement procedure of the catheter. Since the actual catheter position post placement is typically verified, for example by CT or magnetic resonance imaging (MRI), the catheter materials are chosen so as to be visible in such CT and MRI scans. The system includes catheter tubes, preferably a main catheter tube and a micro infusion catheter tube, a stiffening member for placement purposes and a Perifix® connector or other suitable adapter at the proximal end of the catheter system. The infusion syringe or other infusion source, the connectors and any associated tubing are preferably commercially available. The catheter is placed stereotactically on the basis of a planning MRI scan to be made before the positioning. To facilitate exact positioning, a stereotactic planning and navigation software can be used.

As can be seen from the foregoing, the preferred catheter of the present invention has a stepped distal configuration which inhibits backflow along the catheter. In addition, the preferred catheter has a closed loop or quasi-closed loop infusion system that can be filled and primed prior to catheter placement in order to avoid the introduction of air. In addition, the catheter and method of the present invention enhances the anatomic accuracy of the catheter placement, by utilization of a stiffening member during placement. The placement accuracy may be further improved by use of a suitable stereotactic planning software that allows visualizing the expected distribution volume around each catheter based on the local anatomy and tissue properties of the patient. Further, the addition of an MRI tracer, such as gadodiamide, to the active therapeutic, for example topotecan, enables active monitoring of the drug distribution in real time. In a particularly preferred method of the invention, a liposomal formulation of topotecan (and gadodiamide) is associated with an extended residence time in brain and thus, a markedly prolonged drug exposure of the tumor, relative to free topotecan.

What is claimed is:

1. A catheter for delivering an agent from a supply to targeted brain tissue of a mammalian body comprising:
   i. a first elongate tubular member having a proximal opening and a distal end wall,
   ii. a second elongate tubular member adapted for coupling to the supply, the second elongate tubular member having a portion extending through the first elongate tubular member and a distal end secured to and extending beyond the distal end wall of the first tubular member, the first and second tubular members forming a fixed annular cavity between the first tubular member and second tubular member and ending blindly at said distal end wall, and
   iii. a stiffening member having at least a portion disposed within the annular cavity for providing rigidity to and facilitating accurate placement of the distal end relative to the targeted brain tissue in the mammalian body and removable from the annular cavity after such placement without removal of the second elongate tubular member from the mammalian body; wherein the first elongate tubular member and the second elongate tubular member are connected at the distal end wall of the first elongate tubular member so that their lumens do not communicate.

2. The catheter of claim 1 wherein the distal end extends beyond the end wall a distance ranging from 5 to 15 millimeters.

3. The catheter of claim 1 wherein the stiffening member is formed from first and second elongate portions that are separable from each other to permit removal of the stiffening member from the first and second elongate tubular members without decoupling of the second elongate tubular member from the supply so as to enhance delivery of the agent to the targeted brain tissue.

4. The catheter of claim 1 wherein the distal end of the second elongate tubular member is rigid.

5. The catheter of claim 1 wherein the catheter comprises a distal extremity with a step suitable to reduce backflow of fluid along the outer surface of the catheter.

6. The catheter of claim 5, wherein the step suitable to reduce backflow of fluid along the outer surface of the catheter is formed by the distal end wall.

* * * * *